(12) United States Patent
Lee et al.

(10) Patent No.: US 9,649,038 B2
(45) Date of Patent: May 16, 2017

(54) METHOD, MEDIUM, AND APPARATUS FOR MEASURING HEART RATE

(75) Inventors: Hyoungki Lee, Suwon-si (KR); Kiwan Choi, Anyang-si (KR); Sookwon Bang, Seoul (KR)

(73) Assignee: Samsung Electronics Co., Ltd., Gyeonggi-Do (KR)

(*) Notice: Subject to any disclaimer, the term of this patent is extended or adjusted under 35 U.S.C. 154(b) by 2374 days.

(21) Appl. No.: 11/086,412

(22) Filed: Mar. 23, 2005

(65) Prior Publication Data

US 2005/0215913 A1    Sep. 29, 2005

(30) Foreign Application Priority Data

Mar. 23, 2004 (KR) .................... 10-2004-0019626

(51) Int. Cl.
*A61B 5/02* (2006.01)
*A61B 5/024* (2006.01)

(52) U.S. Cl.
CPC .................. *A61B 5/02416* (2013.01)

(58) Field of Classification Search
CPC ................................ A61B 5/02416
USPC ........................................ 600/500
See application file for complete search history.

(56) References Cited

U.S. PATENT DOCUMENTS

| | | | |
|---|---|---|---|
| 5,012,411 A * | 4/1991 | Policastro et al. | ............ 600/485 |
| 5,662,106 A | 9/1997 | Swedlow et al. | |
| 5,830,137 A | 11/1998 | Scharf | |
| 6,018,673 A | 1/2000 | Chin et al. | |
| 6,360,113 B1 * | 3/2002 | Dettling | ........................ 600/322 |
| 6,385,821 B1 | 5/2002 | Modgil et al. | |
| 2002/0045806 A1 | 4/2002 | Baker, Jr. et al. | |
| 2003/0229276 A1 * | 12/2003 | Sarussi et al. | ................ 600/322 |
| 2004/0193063 A1 * | 9/2004 | Kimura et al. | ................ 600/500 |

FOREIGN PATENT DOCUMENTS

| | | |
|---|---|---|
| EP | 0554208 | 1/1993 |
| EP | 1354553 | 4/2003 |
| EP | 1393673 | 8/2003 |
| JP | 11-188019 | 7/1999 |
| KR | 2000-0075056 | 12/2000 |

OTHER PUBLICATIONS

European Search Report issued Aug. 2, 2005.

* cited by examiner

*Primary Examiner* — Christian Jang
(74) *Attorney, Agent, or Firm* — Harness, Dickey & Pierce, P.L.C.

(57) ABSTRACT

A method, medium, and apparatus for measuring a heart rate from blood flow in a blood vessel of a human body part, including: an amplifying circuit receiving a light signal reflected or penetrated from a human body part and generating a multi-stage amplified signal made up of a plurality of signals with a corresponding different gains; and a processor separating the multi-stage amplified signal into a plurality of channel signals having corresponding gains, reconfiguring the light signal using a channel signal selected among the plurality of channel signals and calculating the heart rate from the reconfigured light signal. Accordingly, it is possible to make an accurate measurement of a heart rate by minimizing effects of measuring environments. In addition, the apparatus, method, and medium are resistive to noise resulting from a movement of a human body part by comparing an optimum signal pattern and a correlation coefficient.

20 Claims, 6 Drawing Sheets

METHOD, MEDIUM, AND APPARATUS FOR MEASURING HEART RATE

CROSS-REFERENCE TO RELATED APPLICATIONS

This application claims the benefit of Korean Patent Application No. 10-2004-0019626, filed on Mar. 23, 2004, in the Korean Intellectual Property Office, the disclosure of which is incorporated herein in its entirety by reference.

BACKGROUND OF THE INVENTION

1. Field of the Invention

Embodiments of the present invention relate to methods, media, and apparatuses for measuring a heart rate, and more particularly, to methods, media, and apparatuses for measuring a heart rate by measuring blood flow.

2. Description of the Related Art

Figure 1:
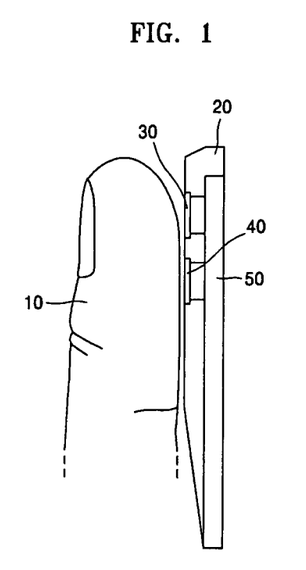
FIG. 1 illustrates an apparatus for measuring a heart rate by using blood flow, according to an embodiment of the present invention.

FIG. 1 illustrates a sampling apparatus 20 for measuring heart rate based on blood flow, as implemented in embodiments of the present invention. In general, the sampling apparatus 20 measures the blood flow, oxygen saturation, or heart rate of a human body, e.g., at a finger, wrist, cheek, or earlobe, by using a photoplethysmography (PPG) sensor.

The sampling apparatus 20 includes an optical transmitting circuit 30, an optical receiving circuit 40, and a processor 50. When infrared or visible light output from the optical transmitting circuit 30 is reflected from a blood vessel, e.g., of a finger 10, the optical receiving circuit 40 detects an amplitude of the reflected light from the blood vessel of the finger 10. The amplitude of the reflected light is proportional to the blood flow in the blood vessel. The processor 50 then measures the heart rate using the reflected light detected by the optical receiving circuit 40.

However, measurement of the heart rate can be affected by the varying of contact pressure between the finger 10 and the sampling apparatus 20, the condition of a capillary vessel in the finger 10, or noise resulting from movement of the finger 10. Thereby resulting in a deteriorating of accuracy in measuring the heart rate.

SUMMARY OF THE INVENTION

Embodiments of the present invention provide methods, media, and apparatuses for measuring a heart rate accurately by using blood flow, irrespective of a varying contact pressure between a body part and a sampling apparatus, the condition of a capillary vessel in the body part, or noise resulting from movement of the body part, for example.

To achieve the above and/or other aspects and advantages, embodiments of the present invention set forth a heart rate measuring system, including an amplifying unit to receive a light signal reflection of a body and to generate a multi-stage amplified signal made up of a plurality of different corresponding signals with different gains, and a processor to separate the multi-stage amplified signal into a plurality of channel signals and to calculate the heart rate from at least one of the channel signals.

The plurality of different signals with different gains may be selectively generated based upon a control signal. In addition, the light signal reflection may be infrared or visible light.

The system may further include an optical transmitting unit to output a light to the body, and a detecting unit to detect a reflected light signal from the body. The detecting unit may include an optical receiving unit to receive a reflected light signal and to detect an amplitude of the reflected light signal, and a filter to filter an output of the optical receiving unit. Further, the detecting unit may include an amplifier to amplify the filtered output of the optical receiving unit.

The amplifying unit may include an amplifier to amplify a difference between a signal input to a first input terminal and a signal input to a second input terminal, a plurality of different resistances, and a multiplexer transmitting a reflected light signal to a corresponding resistance, of the plurality of resistances, according to a control signal output from the processor, wherein each of the plurality of resistances is positioned between the first input terminal and the multiplexer.

The processor may include a first signal reconfiguring unit to separate the multi-stage amplified signal into the plurality of channel signals, to divide each of the plurality of channel signals into segments, based on peak values of each corresponding channel signal, and to generate a first reconfigured light signal including a channel signal selected among the plurality of channel signals with regard to each segment, a second signal reconfiguring unit to calculate a correlation coefficient from the first reconfigured light signal and a basic pattern and generating a second reconfigured light signal using the correlation coefficient, and a heart rate calculating unit to compare the second reconfigured light signal with a reference correlation coefficient, and to calculate the heart rate based on a result of the comparison.

Each of the segments may be a sector between a central point of an i-th peak point and a (i+1)-th peak point and a central point of a (i+1)-th peak point and a (i+2)-th peak point. The one channel signal may have an unsaturated highest peak value in a corresponding segment.

The processor may include a signal reconfiguring unit to separate the multi-stage amplified signal into the plurality of channel signals, to divide each of the plurality of channel signals into segments, based on peak values of each corresponding channel signal, and to generate a reconfigured light signal including a channel signal selected among the plurality of channel signals with regard to each segment, and a heart rate calculating unit to compare the reconfigured signal with a reference correlation coefficient, and to calculate the heart rate based on a result of the comparison. Each of the segments may be a sector between a central point of an i-th peak point and a (i+1)-th peak point and a central point of a (i+1)-th peak point and a (i+2)-th peak point, and the one channel signal may have an unsaturated highest peak value in a corresponding segment.

The reflected light signal may be a measure of light reflected off a blood vessel within the body and/or a measure of light permeability of the blood vessel. In addition, the body may be a human body.

To achieve the above and/or other aspects and advantages, embodiments of the present invention set forth a heart rate measuring system, including a detecting unit to detect a light signal reflection from a body, and a processor to receive the reflection light signal from the detecting unit, to generate a reconfigured signal based on a correlation between the reflection light signal and a basic pattern, and to calculate the heart rate from the reconfigured signal. The processor may include a signal reconfiguring unit to calculate a correlation coefficient from the reflection light signal and the basic pattern and to generate the reconfigured signal using the correlation coefficient, and a heart rate calculating unit to compare the reconfigured signal with a reference correlation coefficient, and to calculate the heart rate based on a signal obtained from a result of the comparison.

To achieve the above and/or other aspects and advantages, embodiments of the present invention set forth a method of measuring a heart rate, including receiving a light signal reflection from a body, generating a multi-stage amplified signal by separately amplifying the reflected light signal with a plurality of corresponding different gains, separating the multi-stage amplified signal into a plurality of channel signals having corresponding gains, and calculating the heart rate based on at least one of the channel signals.

The generating of the multi-stage amplified signal may include transmitting the reflected light signal to a first input terminal of an amplifier through channels, among a plurality of channels, based on a control signal, to generate the channel signals, respectively, and amplifying a difference between the reflected light signal input to the first input terminal and a signal input to a second input terminal.

The method may further include dividing each of the plurality of channel signals into segments, and generating a first reconfigured light signal including a channel signal selected among the plurality of channel signals with regard to each segment, and generating a second reconfigured light signal based on a correlation between the first reconfigured signal and a basic pattern.

In addition, the method may include dividing each of the plurality of channel signals into segments, and generating a reconfigured signal including a channel signal selected among the plurality of channel signals with regard to each segment.

To achieve the above and/or other aspects and advantages, embodiments of the present invention set forth a method of measuring a heart rate, including receiving a light signal reflection from a body, generating a reconfigured light signal based on a correlation between the reflected light signal and a basic pattern, and calculating the heart rate from the reconfigured signal.

To achieve the above and/or other aspects and advantages, embodiments of the present invention set forth a medium including computer readable code implementing a method of measuring a heart rate, including receiving a light signal reflection from a body, generating a multi-stage amplified signal by separately amplifying the reflected light signal with a plurality of corresponding different gains, separating the multi-stage amplified signal into a plurality of channel signals, dividing each of the plurality of channel signals into segments, and generating a first reconfigured signal including a channel signal selected among the plurality of channel signals with regard to each segment, generating a second reconfigured signal based on a correlation between the first reconfigured signal and a basic pattern, and calculating the heart rate from the second reconfigured signal.

To achieve the above and/or other aspects and advantages, embodiments of the present invention set forth a medium including computer readable code implementing a method of measuring a heart rate, including receiving a light signal reflection from a body, generating a multi-stage amplified signal by separately amplifying the reflected light signal, with a plurality of corresponding different gains, separating the multi-stage amplified signal into a plurality of channel signals, dividing each of the plurality of channel signals into segments, and generating a reconfigured signal including a channel signal selected among the plurality of channel signals with regard to each segment, and calculating the heart rate from the reconfigured signal.

To achieve the above and/or other aspects and advantages, embodiments of the present invention set forth a medium including computer readable code implementing a method of measuring a heart rate, including receiving a light signal reflection from a body, generating a reconfigured signal based on a correlation between the reflected light signal and a basic pattern, and calculating the heart rate from the reconfigured signal.

Additional aspects and/or advantages of the invention will be set forth in part in the description which follows and, in part, will be apparent from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE PREFERRED EMBODIMENTS

Reference will now be made in detail to the embodiments of the present invention, examples of which are illustrated in the accompanying drawings, wherein like reference numerals refer to the like elements throughout. The embodiments are described below to explain the present invention by referring to the figures.

Figure 2:
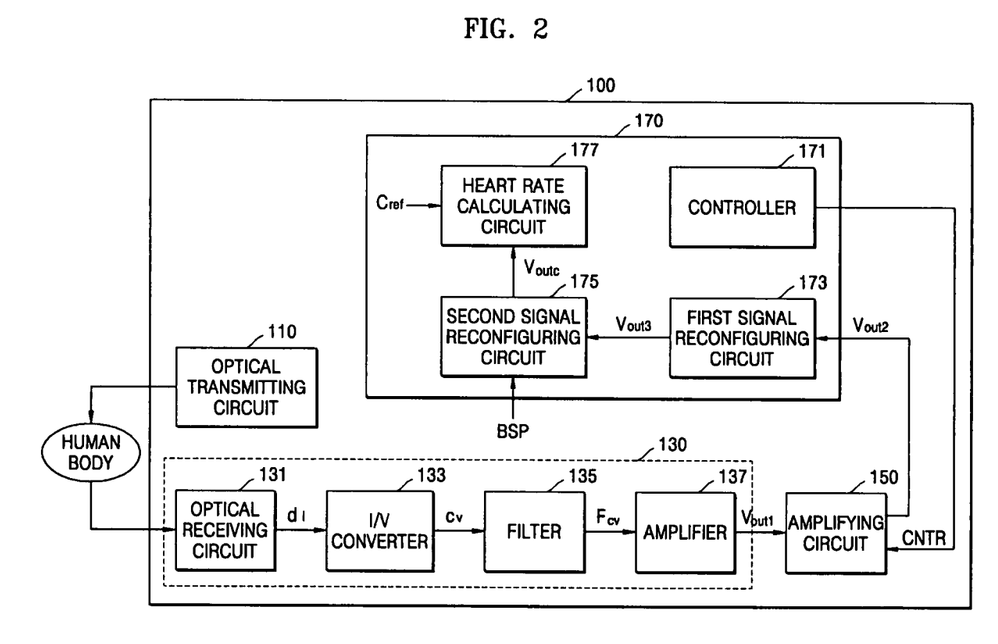
FIG. 2 illustrates a block diagram for measuring a heart rate by using blood flow, according to an embodiment of the present invention.

FIG. 2 illustrates a block diagram showing an apparatus 100 for measuring a heart rate by using blood flow, according to an embodiment of the present invention. The apparatus 100 may be implemented with semiconductor chips, and may include an optical transmitting circuit 110, a detecting circuit 130, an amplifying circuit 150, and a processor 170. As noted above, in embodiments of the present invention, the sensing apparatus 20 of FIG. 1 may also correspond to apparatus 100 of FIG. 2, for example.

The optical transmitting circuit 110 generates a light signal and outputs the light signal to a body part, e.g., a human body part. Examples of such a light signal can include infrared or visible light, but are not limited thereto.

The detecting circuit 130 receives the infrared or visible light reflected or penetrated from the body part, particularly a blood vessel of the body part, filters the received light signal, amplifies the filtered light signal, and outputs the amplified light signal $V_{out1}$ to an amplifying circuit 150. The detecting circuit 130 can include an optical receiving circuit 131, an I/V converter 133, a filter 135, and an amplifier 137.

The optical receiving circuit 131 detects an amplitude of the infrared or visible light reflected or penetrated from the body part, and generates a current $d_i$ based on the detected amplitude. The amplitude of the infrared or visible light received by the optical receiving circuit 131 varies according to a thickness of a blood vessel of the body part. For instance, when the infrared or visible light output from the optical transmitting circuit 110 is input to the body part, during expansion of a blood vessel, the blood vessel absorbs the infrared or visible light. Thus, the amplitude of the infrared or visible light reflected or penetrated may be reduced compared to a reference amplitude of a non-expanded blood vessel.

The I/V converter 133 receives the current $d_i$ from the optical receiving circuit 131 and generates a voltage $C_v$ corresponding to the current $d_i$. In other words, the I/V converter 133 acts as a current/voltage converter.

The filter 135 is preferably implemented with a lowpass filter. The filter 135 receives the voltage $C_v$ from the I/V converter 133, removes high-frequency noise from the voltage $C_v$, and outputs the result $F_{cv}$. The amplifier 137 receives the voltage $F_{cv}$ output from the filter 135, amplifies the voltage $F_{cv}$, and outputs the result as $V_{out1}$.

The amplifying circuit 150 generates a multi-stage amplified signal $V_{out2}$ made up of multiple signals having "n" different gains, in response to a control signal CNTR output from a controller 171 of the processor 170.

Figure 3:
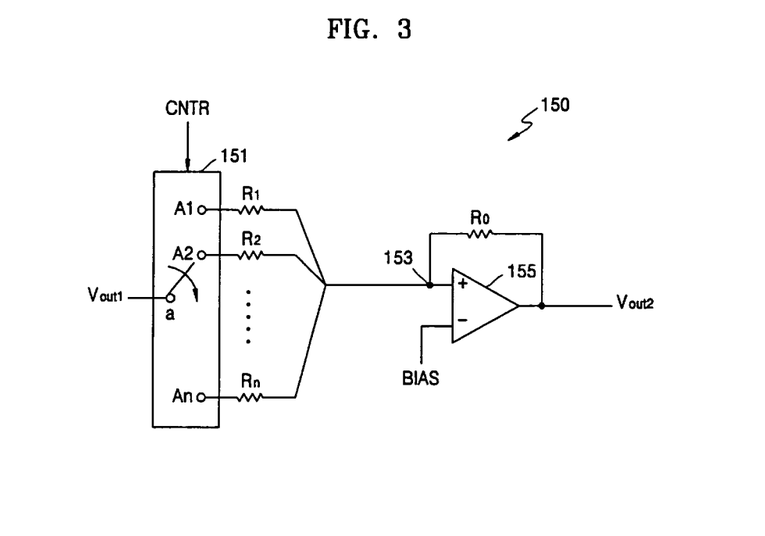
FIG. 3 illustrates a circuit diagram of an amplifying circuit for FIG. 2, according to an embodiment of the present invention.

FIG. 3 illustrates a circuit diagram of an amplifying circuit 150 for the apparatus of FIG. 2. The amplifying circuit 150, for example, may include an n-channel multiplexer 151, a plurality of resistors $R_1$ through $R_n$, a comparator 155, and a resistor $R_0$.

As illustrated in FIG. 3, the n-channel multiplexer 151 transmits the voltage $V_{out1}$, output from the amplifier 137, to each of corresponding terminals A1 through An, based on the control signal CNTR. Each of the resistors $R_1$ through $R_n$ is connected between each of the corresponding terminals A1 through An and a node 153. The resistances of the individual resistors $R_1$ through $R_n$ are preferably all different from one another, though this is not necessary. The pairing of each of the terminals A1 through An and each of the resistors $R_1$ through $R_n$ can be considered a channel.

The resistor $R_0$ is connected between node 153 and an output terminal of the comparator 155. The comparator 155 receives a bias voltage BIAS and a voltage of the node 153, amplifies a difference between the received voltages, and outputs the result as $V_{out2}$. The comparator 155 and the resistor $R_0$ may be replaced with a single OP amp having a feedback resistor $R_0$, for example.

When the voltage $V_{out1}$, output from the amplifier 137, is applied to the comparator 155 through the terminal A1 and the resistor $R_1$, based on the control signal CNTR, the voltage gain of the amplifying circuit 150 is proportional to $-(R_0/R_1)$. In addition, when the voltage $V_{out1}$ is applied to the comparator 155 through the terminal An and the resistor $R_n$, based on the control signal CNTR, the voltage gain of the amplifying circuit 150 is proportional to $-(R_0/R_n)$, exemplified by Equation 1 below.

$$\text{Gain} = -\frac{R_0}{R_n} \qquad \text{Equation 1}$$

Here, "n" is a natural number, according to this embodiment of the present invention.

Figure 4:
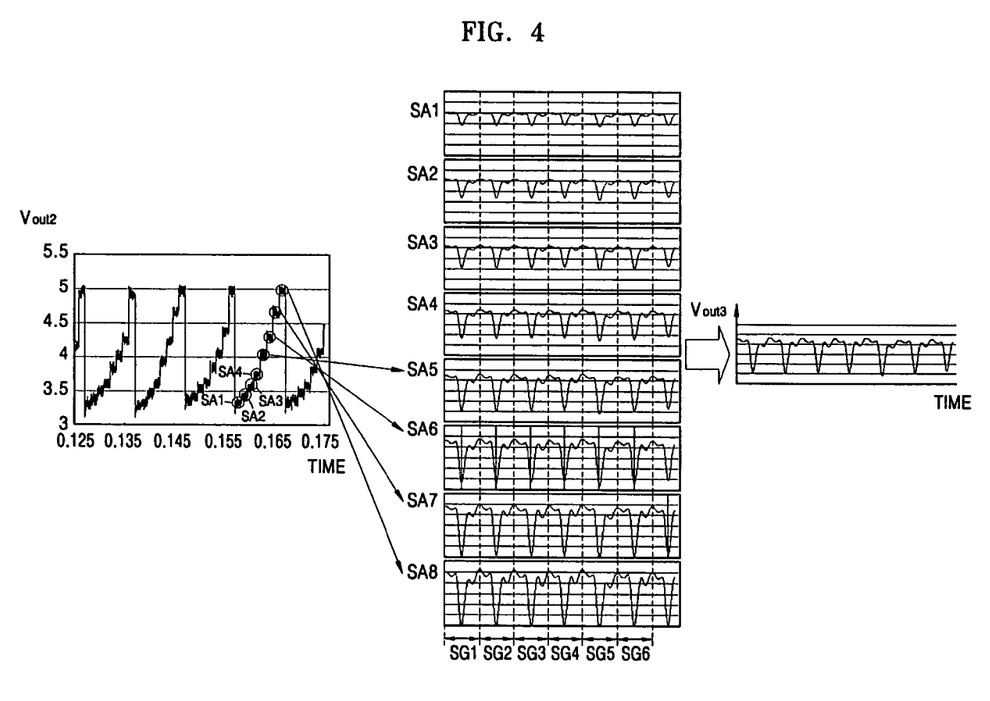
FIG. 4 illustrates input and output waveforms of a first signal reconfiguring circuit for the apparatus of FIG. 2, according to an embodiment of the present invention.

FIG. 4 illustrates input and output waveforms of a first signal reconfiguring circuit 173 for the apparatus of FIG. 2. Referring to FIGS. 3 and 4, the output voltage $V_{out2}$ of the amplifying circuit 150 is a signal obtained by superimposing a plurality of signals SA1 through SA8 having different gains. For convenience' sake, FIG. 4 illustrates an output signal $V_{out2}$ of the amplifying circuit 150 made possible by an eight-channel multiplexer 151. In the illustrated embodiment of FIG. 4, the number of resistors and terminals is also 8, respectively.

When the FIG. 3 illustrated terminal "a" is selectively connected, e.g., sequentially, to the terminals A1 through An (n=8) in each cycle, the output signal $V_{out2}$ of the amplifying circuit 150, for this embodiment, corresponds to the illustrated $V_{out2}$ shown in FIG. 4. Therefore, the output signal $V_{out2}$ of the amplifying circuit 150 for each cycle is obtained and superimposed (or summed) having "n" different gains according to the exemplary Equation 1.

As illustrated in FIG. 4, the output signal $V_{out2}$ of the amplifying circuit 150 can be separated into signals SA1 through SA8. For example, SA1 can represent the output signal $V_{out2}$ of the amplifying circuit 150 when the voltage $V_{out1}$, output from the amplifier 137, is applied to the comparator 155 through the terminal A1 and the resistor R1. As Illustrated, SAn (where "n" is 2 through 8) represents the output signal $V_{out2}$ of the amplifying circuit 150 when the voltage $V_{out1}$ is applied to the comparator 155 through the terminal An (where "n" is 2 through 8) and the resistor $R_n$ (where "n" is 2 through 8), for example.

The processor 170, illustrated in FIG. 2, may include a controller 171, a first signal reconfiguring circuit 173, a second signal reconfiguring circuit 175, and a heart rate calculating circuit 177. The processor 170 may also be implemented with semiconductor chips. In another embodiment, the processor 170 may include, rather, the controller 171, the first signal reconfiguring circuit 173, and the heart rate calculating circuit 177. According to this embodiment, the output signal $V_{out3}$ of the first signal reconfiguring circuit 173 can be directly applied to the heart rate calculating circuit 177. In still another embodiment, the processor 170 may include, alternately, the controller 171, the second signal reconfiguring circuit 175, and the heart rate calculating circuit 177. According to this embodiment, the output signal $V_{out1}$ of the amplifier 137 may be directly applied to the second signal reconfiguring circuit 175.

The controller 171 may provide the control signal CNTR to the amplifying circuit 150 for controlling an operation of the n-channel multiplexer 151, for example.

The first signal reconfiguring circuit 173 may receive the output signal $V_{out2}$ of the amplifying circuit 150, store the received signals, detect peak values of the stored output signal $V_{out2}$ which are peak values of heart rate signals, and divide adjacent peak values in a unit of segments, for example. According to an embodiment of the present invention, the first signal reconfiguring circuit 173 may select a single signal having an optimum amplitude in each segment (SG1 through SG6 in FIG. 4), and generate a first reconfigured signal $V_{out3}$ corresponding to the selected segments of the selected signals. Each of the selected signals has an unsaturated highest peak value in each segment (SG1 through SG6 in FIG. 4). In addition, since the signals of the individual segments may be amplified with different gains, each of the signals selected in the individual segments can be normalized by dividing each of the signals by their respective gains, when the first reconfigured signal is generated.

As only an example, assuming that the signal SA6 is selected for segment SG1, the signal SA7 is selected for segment SG2, the signal SA5 is selected for segment SG3, the signal SA4 is selected for segment SG4, the signal SA8 is selected for segment SG5, and the signal SA1 is selected for segment SG6, the first signal reconfiguring circuit 173 can normalize each of the signal portions selected for the segments SG1 through SG6, and output a reconfigured signal $V_{out3}$ resulting from the normalization.

Figure 5:
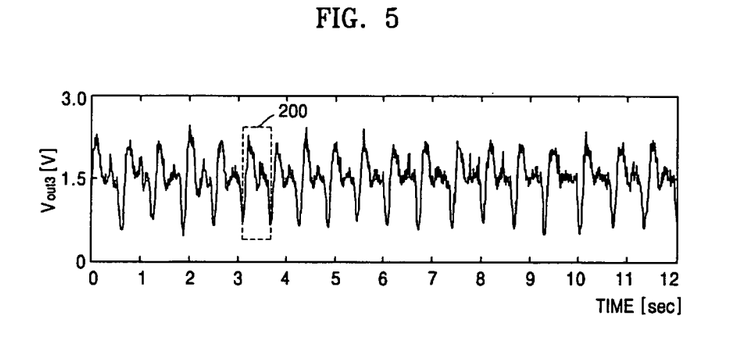
FIG. 5 illustrates an output waveform of a first signal reconfiguring circuit for the apparatus of FIG. 2, according to an embodiment of the present invention.
Figure 6:
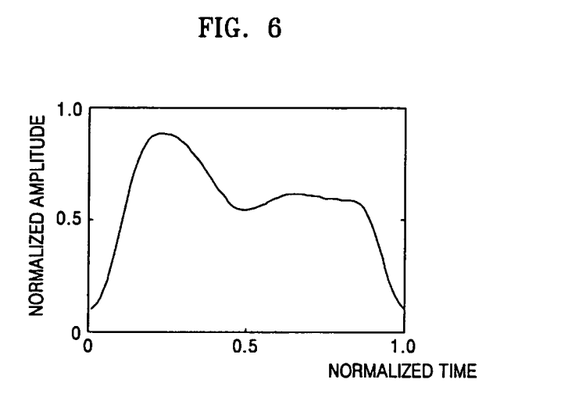
FIG. 6 illustrates a basic pattern of a waveform used for calculating a correlation coefficient in a second signal reconfiguring circuit for the apparatus of FIG. 2, according to an embodiment of the present invention.

The second signal reconfiguring circuit 175 may receive the output signal $V_{out3}$ from the first signal reconfiguring circuit 173 in FIG. 5, sample a signal 200 corresponding to one segment in the signal $V_{out3}$, normalize the sampled signal 200, generate a basic pattern, e.g., as shown in FIG. 6, and store the generated basic pattern. In another embodiment, the second signal reconfiguring circuit 175 may receive and store a basic pattern BSP, e.g., a reference basic pattern, as shown in FIG. 6, from outside of the second signal reconfiguring circuit 175. The second signal reconfiguring circuit 175 may receive the basic pattern BSP and the output signal $V_{out3}$ of the first signal reconfiguring circuit 173, estimate a correlation coefficient C between the basic pattern BSP and the signal of each segment in the output signal $V_{out3}$, and output a second reconfigured signal $V_{outc}$ having the estimated correlation coefficient C in each segment to the heart rate calculating circuit 177.

The correlation coefficient C may be estimated through the below Equation 2, for example.

$$C = \frac{\frac{1}{N+1}\sum_{i=0}^{N}(x_{k(i)} - \bar{x})(b_i - \bar{b})}{\sigma_x \sigma_b},$$

$$k(i) = \frac{(N-i)P_n + iP_{n+1}}{N},$$

Equation 2 where $X_{k(i)}$ denotes a k(i)-th signal, $b_i$ denotes an i-th basic pattern having a single cycle 0 through N, $\sigma_x$ and $\sigma_b$ denote standard deviations of $\bar{x}$ and $\bar{b}$, respectively, x and b denote mean values of x and b, respectively, $P_n$ denotes a n-th peak point, $P_{n+1}$ denotes a (n+1)-th peak point, and i denotes a natural number, according to this embodiment of the present invention.

Therefore, each of the segments SG1 through SG6 is a sector between a central point of an n-th peak point and a (n+1)-th peak point and a central point of a (n+1)-th peak point and a (n+2)-th peak point. However, the sector of each of the segments, according to embodiments of the present invention, is not limited to the sector as defined above.

The first signal reconfiguring circuit 173 may separate the output signal $V_{out2}$ of the amplifying circuit 150, according to channels, detect a peak value of a signal in each of the channels, allot a sector between neighboring peak values to a segment, selects signals allotted to each segment according to a predetermined standard, reconfigure the selected signals, and output the result $V_{out3}$. The predetermined standard is a standard for obtaining a signal having an unsaturated highest peak value.

The heart rate calculating circuit 177 may receive the second reconfigured signal $V_{outc}$ having the correlation coefficient C and a reference correlation coefficient $C_{ref}$, compare the correlation coefficient C and the reference correlation coefficient $C_{ref}$ and calculate the heart rate from a signal having the correlation coefficient C larger than the reference correlation coefficient $C_{ref}$, according to the comparison result. The reference correlation coefficient $C_{ref}$ may be input from outside the apparatus 100, or be already stored in a memory of the heart rate calculating circuit 177. For instance, when the correlation coefficient C has a range of 0 through 1, the correlation coefficient C may be close to 1 for a normal signal, and the correlation coefficient C may be close to 0 for a signal with noise. However, a range of the correlation coefficient C may be diversely set.

Figure 7:
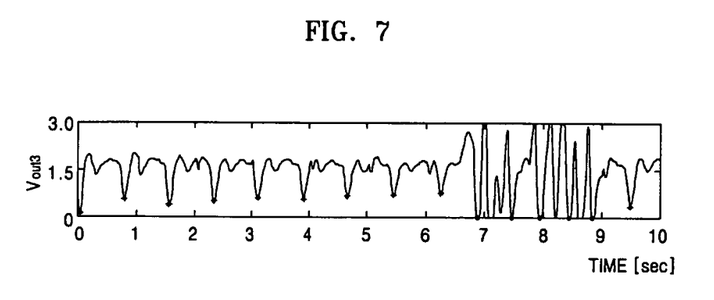
FIG. 7 illustrates an output waveform of a first signal reconfiguring circuit including noise.
Figure 8:
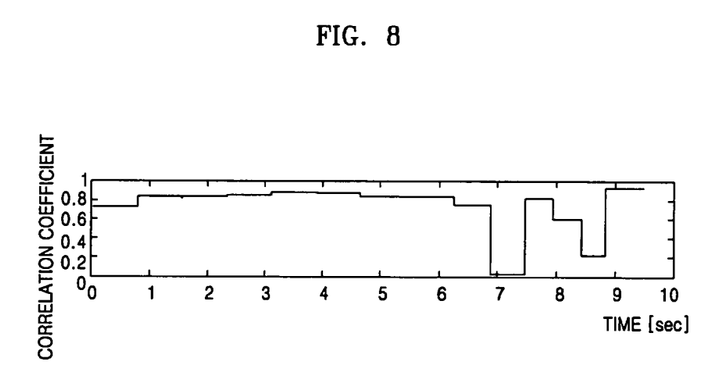
FIG. 8 illustrates a correlation coefficient of the output waveform in FIG. 7, according to an embodiment of the present invention.

FIG. 7 illustrates an output waveform of a first signal reconfiguring circuit 173 including noise, and FIG. 8 illustrates a correlation coefficient of the output waveform in FIG. 7, according to an embodiment of the present invention.

Referring FIGS. 2, 7, and 8, when noise is resident in the output signal $V_{out3}$ of the first signal reconfiguring circuit 173, the correlation coefficient C will be close to 0. Therefore, the heart rate calculating circuit 177 will only count signals having a correlation coefficient C greater than the reference correlation coefficient $C_{ref}$, among the output signal $V_{outc}$ of the second signal reconfiguring circuit 175, but would not count different signals which can be considered as having too much noise. Therefore, even though noise may be resident in the output signal $V_{out3}$ of the first signal reconfiguring circuit 173, the heart rate calculating circuit 177 can still count the heart rate by excluding the noise by using the correlation, and output the result to a display (not shown).

Embodiments of the present invention can further be implemented through computer readable code/instructions, e.g., a software program, stored/transferred through a medium, e.g., a computer-readable recording medium. The medium can be any data storage/transmitting device that can store/transmit data which can be thereafter be implemented by a computer system. Examples of media may include read-only memory (ROM), random-access memory (RAM), CD-ROMs, magnetic tapes, floppy disks, optical data storage devices, and carrier waves (such as data transmission through the Internet), for example. The medium, or media, can also be distributed over network-coupled computer systems so that the computer-readable code is stored/transferred and/or executed in a distributed fashion. Also, functional programs, codes, and code segments for accomplishing embodiments of the present invention can be easily construed by programmers skilled in the art to which the present invention pertains.

The method, medium, and apparatus, according to embodiments of the present invention, can be used in a portable heart rate measuring instrument capable of measuring heart rate by using blood flow, e.g., an MP3 player having a function of measuring the amount of exercise, a stress measuring instrument, a calorie consumption measuring instrument or the like.

According to embodiments of the present invention, since the corresponding methods, media, and apparatuses for measuring heart rate by using blood flow do not require an additional operation of regulating a gain, it is possible to reduce the time required for measuring the heart rate.

In addition, the methods, media, and apparatuses, according to embodiments of the present invention, for measuring a heart rate by using blood flow is resistive to noise resulting from a movement of a body part by comparing an optimum signal pattern with a correlation coefficient.

In addition, the methods, media, and apparatuses, according to embodiments of the present invention, for measuring a heart rate by using blood flow can prevent performance degradation resulting from a varying contact pressure between the body part and the apparatus.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A heart rate measuring system, comprising:
   an optical transmitting unit configured to output a light signal to a body;
   a detecting unit configured to detect a reflected light signal from the body in response to the light signal output to the body;
   an amplifying unit configured to receive the reflected light signal of the body and to generate with the reflected light signal, a multi-stage amplified signal made up of a plurality of different corresponding signals with different gains, the amplifying unit including a multiplexer; and
   a processor configured to separate the multi-stage amplified signal from the amplifying unit into a plurality of channel signals having gains respectively corresponding to the different gains, to reconfigure the light signal using at least one of the plurality of channel signals, and to calculate the heart rate based on a correlation coefficient which is estimated by using the reconfigured light signal and a basic pattern,
   wherein the amplifying unit further comprises an amplifier configured to amplify a difference between a signal input to a first input terminal and a signal input to a second input terminal, the first input terminal is connected to one of each of different resistances which corresponds to each of the different gains, in response to a control signal from the processor, and the amplifying unit is configured to generate the multi-stage amplified signal by superimposing the plurality of different corresponding signals with different gains.

2. The system of claim 1, wherein the plurality of different corresponding signals with different gains are selectively generated based upon the control signal.

3. The system of claim 1, wherein the light signal reflection is infrared or visible light.

4. The system of claim 1, wherein the detecting unit comprises:
   an optical receiving unit configured to receive the reflected light signal and to detect an amplitude of the reflected light signal; and
   a filter configured to filter an output of the optical receiving unit.

5. The system of claim 4, wherein the detecting unit further comprises an amplifier configured to amplify the filtered output of the optical receiving unit.

6. The system of claim 1, wherein the reflected light signal is detected by measuring light signal reflected off a blood vessel within the body and/or by measuring light signal permeability of the blood vessel.

7. The system of claim 1, wherein the body is a human body.

8. The system of claim 1, wherein the separated plural channel signals each correspond to a respective one of the plurality of different corresponding signals and a respective one of the different gains.

9. The system of claim 1, wherein
   the amplifying unit separately amplifies the received light signal reflection of the body three or more times using respectively different gains to generate the multi-stage amplified signal made up of three or more different corresponding signals, as the plurality of different corresponding signals, and
   the processor separates the multi-stage amplified signal into three or more separated channel signals respectively corresponding to the three or more different corresponding signals.

10. A heart rate measuring system, comprising:
    an optical transmitting unit configured to output a light signal to a body;
    a detecting unit configured to detect a reflected light signal from the body in response to the light signal output to the body;
    an amplifying unit configured to receive the reflected light signal of the body and to generate with the reflected light signal, a multi-stage amplified signal made up of a plurality of different corresponding signals with different gains; and
    a processor configured to separate the multi-stage amplified signal from the amplifying unit into a plurality of channel signals and to calculate the heart rate from at least one of the channel signals,
    wherein the amplifying unit comprises:
    an amplifier configured to amplify a difference between a signal input to a first input terminal and a signal input to a second input terminal;
    a plurality of different resistances; and
    a multiplexer configured to transmit the reflected light signal to a corresponding resistance, of the plurality of resistances, according to a control signal output from the processor,
    wherein each of the plurality of resistances is positioned between the first input terminal and the multiplexer,
    wherein the first input terminal is selected among the plurality of terminals having different resistances, in response to the control signal from the processor, and the amplifying unit is configured to generate the multi-stage amplified signal by superimposing the plurality of different corresponding signals with different gains.

11. A heart rate measuring system, comprising:
    an optical transmitting unit configured to output a light signal to a body;
    a detecting unit configured to detect a reflected light signal from the body in response to the light signal output to the body;
    an amplifying unit configured to receive the reflected light signal of the body and to generate with the reflected light signal, a multi-stage amplified signal made up of a plurality of different corresponding signals with different gains, the amplifying unit including a multiplexer; and
    a processor configured to separate the multi-stage amplified signal from the amplifying unit into a plurality of channel signals and to calculate the heart rate from at least one of the channel signals,
    wherein the processor comprises:
    a controller configured to output a control signal to the multiplexer of the amplifying unit,
    a first signal reconfiguring unit configured to separate the multi-stage amplified signal into the plurality of channel signals, to divide each of the plurality of channel signals into segments, based on peak values of each corresponding channel signal, and to generate a first reconfigured light signal including a channel signal selected among the plurality of channel signals with regard to each segment;

a second signal reconfiguring unit configured to calculate a correlation coefficient from the first reconfigured light signal and a basic pattern and generating a second reconfigured light signal using the correlation coefficient; and a heart rate calculating unit configured to compare the second reconfigured light signal with a reference correlation coefficient, and to calculate the heart rate based on a result of the comparison, wherein the amplifying unit further comprises an amplifier configured to amplify a difference between a signal input to a first input terminal and a signal input to a second input terminal, the first input terminal is connected to one of each of different resistances which corresponds to each of the different gains, in response to the control signal from the processor, and the amplifying unit is configured to generate the multi-stage amplified signal by superimposing the plurality of different corresponding signals with different gains.

12. The system of claim 11, wherein each of the segments is a sector between a central point of an i-th peak point and a (i+1)-th peak point and a central point of a (i+1)-th peak point and a (i+2)-th peak point.

13. The system of claim 11, wherein the channel signal has an unsaturated highest peak value in a corresponding segment.

14. A heart rate measuring system, comprising:
an optical transmitting unit configured to output a light signal to a body;
a detecting unit configured to detect a reflected light signal from the body in response to the light signal output to the body;
an amplifying unit configured to receive the reflected light signal of the body and to generate with the reflected light signal, a multi-stage amplified signal made up of a plurality of different corresponding signals with different gains, the amplifying unit including a multiplexer; and
a processor configured to separate the multi-stage amplified signal from the amplifying unit into a plurality of channel signals and to calculate the heart rate from at least one of the channel signals,
wherein the processor comprises:
a controller configured to output a control Signal to the multiplexer of the amplifying unit,
a signal reconfiguring unit configured to separate the multi-stage amplified signal into the plurality of channel signals, to divide each of the plurality of channel signals into segments, based on peak values of each corresponding channel signal, and to generate a reconfigured light signal including a channel signal selected among the plurality of channel signals with regard to each segment; and
a heart rate calculating unit configured to compare the reconfigured light signal with a reference correlation coefficient, and to calculate the heart rate based on a result of the comparison,
wherein the amplifying unit further comprises an amplifier configured to amplify a difference between a signal input to a first input terminal and a signal input to a second input terminal, the first input terminal is connected to one of each of different resistances which corresponds to each of the different gains, in response to the control signal from the processor, and the amplifying unit is configured to generate the multi-stage amplified signal by superimposing the plurality of different corresponding signals with different gains.

15. The system of claim 14, wherein each of the segments is a sector between a central point of an i-th peak point and a (i+1)-th peak point and a central point of a (i+1)-th peak point and a (i+2)-th peak point.

16. The system of claim 14, wherein the channel signal has an unsaturated highest peak value in a corresponding segment.

17. A method of measuring a heart rate, comprising:
outputting a light signal to a body;
detecting a reflected light signal from the body in response to the light signal output to the body;
generating a light signal by converting the current to a voltage;
generating with the reflected light signal, by an amplifying unit, a multi-stage amplified signal made up of a plurality of different corresponding signals with different gains, the amplifying unit including a multiplexer;
separating the multi-stage amplified signal from the amplifying unit into a plurality of channel signals having gains respectively corresponding to the different gains;
reconfiguring the light signal using at least one of the plurality of channel signals; and
calculating, by a processor, the heart rate based on a correlation coefficient which is estimated by using the reconfigured light signal and a basic pattern, the processor including a controller and a heart rate calculating unit, the controller configured to output a control signal to the multiplexer of the amplifying unit, the heart rate calculating unit configured to receive the reconfigured light signal and a reference correlation coefficient,
wherein the amplifying unit further comprises an amplifier configured to amplify a difference between a signal input to a first input terminal and a signal input to a second input terminal, the first input terminal is connected to one of each of different resistances which corresponds to each of the different gains, in response to the control signal from the processor, and the amplifying unit is configured to generate the multi-stage amplified signal by superimposing the plurality of different corresponding signals with different gains.

18. The method of claim 17, further comprising:
dividing each of the plurality of channel signals into segments, and generating a reconfigured signal including a channel signal selected among the plurality of channel signals with regard to each segment.

19. A method of measuring a heart rate, comprising:
outputting a light signal to a body;
detecting a reflected light signal from the body in response to the light signal output to the body;
generating a light signal by converting the current to a voltage;
generating with the reflected light signal, by an amplifying unit, a multi-stage amplified signal made up of a plurality of different corresponding signals with different gains, the amplifying unit including a multiplexer;
separating the multi-stage amplified signal from the amplifying unit into a plurality of channel signals; and
calculating, by a processor, the heart rate from at least one of the channel signals, the processor including a controller, a signal reconfiguring unit, and a heart rate calculating unit, the controller configured to output a control signal to the multiplexer of the amplifying unit, the signal reconfiguring unit configured to receive the multi-stage amplified signal and a basic pattern and to generate a reconfigured light signal, the heart rate calculating unit configured to receive the reconfigured light signal and a reference correlation coefficient, wherein the generating of the multi-stage amplified signal comprises:

transmitting the reflected light signal to a first input terminal of the multiplexer through channels, among the plurality of channels, based on the control signal, to generate the channel signals, respectively; and amplifying a difference between the reflected light signal input to the first input terminal and a signal input to a second input terminal, wherein the first input terminal is selected among the plurality of terminals having different resistances, in response to the control signal from the processor, and the amplifying unit is configured to generate the multi-stage amplified signal by superimposing the plurality of different corresponding signals with different gains.

20. A method of measuring a heart rate, comprising:

outputting a light signal to a body;

detecting a reflected light signal from the body in response to the light signal output to the body;

generating with the reflected light signal, by an amplifying unit, a multi-stage amplified signal made up of a plurality of different corresponding signals with different gains, the amplifying unit including a multiplexer;

separating the multi-stage amplified signal from the amplifying unit into a plurality of channel signals;

dividing each of the plurality of channel signals into segments, and generating a first reconfigured light signal including a channel signal selected among the plurality of channel signals with regard to each segment;

generating a second reconfigured light signal based on a correlation between the first reconfigured signal and a basic pattern; and calculating, by a processor, the heart rate from the second reconfigured light signal, the processor including a controller and a heart rate calculating unit, the controller configured to output a control signal to the multiplexer of the amplifying unit, the heart rate calculating unit configured to receive the second reconfigured light signal and a reference correlation coefficient, wherein the amplifying unit further comprises an amplifier configured to amplify a difference between a signal input to a first input terminal and a signal input to a second input terminal, the first input terminal is connected to one of each of different resistances which corresponds to each of the different gains, in response to the control signal from the processor, and the amplifying unit is configured to generate the multi-stage amplified signal by superimposing the plurality of different corresponding signals with different gains.

* * * * *